(12) United States Patent
Liang et al.

(10) Patent No.: US 6,391,261 B1
(45) Date of Patent: May 21, 2002

(54) DEVICE FOR DETECTING ANALYTES RELATED TO SAMPLE PH

(75) Inventors: Greg Liang; Thomas Foley, both of Rancho Cucamonga, CA (US)

(73) Assignee: Lifepoint, Inc., Rancho Cucamonga, CA (US)

(*) Notice: Subject to any disclaimer, the term of this patent is extended or adjusted under 35 U.S.C. 154(b) by 0 days.

(21) Appl. No.: 09/549,725

(22) Filed: Apr. 14, 2000

(51) Int. Cl.$^7$ ................................................ G01N 33/48
(52) U.S. Cl. ........................ 422/58; 422/61; 436/169; 436/816; 436/901
(58) Field of Search ...................... 422/56–61; 436/164, 436/169, 816, 901

(56) References Cited

U.S. PATENT DOCUMENTS

| | | | |
|---|---|---|---|
| 4,943,522 A | | 7/1990 | Eisinger et al. |
| 5,069,878 A | * | 12/1991 | Ehrenkranz ................... 422/61 |
| 5,155,022 A | | 10/1992 | Naqui et al. |
| 5,501,985 A | * | 3/1996 | Baugher et al. .............. 422/56 |
| 5,559,041 A | | 9/1996 | Kang et al. |
| 5,591,645 A | | 1/1997 | Rosenstein |
| 5,602,040 A | | 2/1997 | May et al. |
| 5,714,341 A | * | 2/1998 | Thieme et al. ................. 422/56 |
| 5,726,062 A | * | 3/1998 | Numa t al. .................... 422/61 |
| 5,989,840 A | * | 11/1999 | D'Angelo et al. ............. 422/56 |

OTHER PUBLICATIONS

Hall, Brad J., et al., Determination of Cannibinoids in Water and Human Saliva by Solid–Phase Microextraction and Quadrupole Ion Trap Gas Chromatography/Mass Spectrometry, Anal. Chem., 70: 1788–96 (1998).

Jusko, et al ., Pharmacokinetic Principles of Drug Distribution in Saliva, Ann. N. Y. Acad. Sci., 694: 36–47 (1993).

Kato, Kenichi, et a;., Cocaine and Metabolite Excretion in Saliva under Stimulated and Nonstimulated Conditions, J. Ana;. Toxicol., 17 (6):321–388 (1993).

Kopecky, E. et al., Correlation of Morphine Sulfate in Blood Plasma and Saliva in Pediatric Patients, Ther. Drug Monitoring, 19 No. 5: 530–34 (1997).

Leonard, J. et al., Correlation of Buccal Mucosal Transudate Collected with a Buccal Swab and Urine Levels of Cocaine, J. Addictive Beh., 13 No. 1: 27–31 (1994).

Malamud, D., Saliva as a Diagnostic Fluid, Br. Med. J., 305: 207–208 (1990).

Mandel, I. D., The Diagnostic Uses of Saliva, J. Oral Pathol. Med., 19: 119–125 (1990).

Mandel, I. D., "Salivary Diagnosis: Promises, Promises," in Malamud D., and Tabak, L. (ed.) Saliva as a Diagnostic Fluid, Annals of the New York Academy of Sciences, 694: 1–8 (1993).

Mendelson, John, et al., Bioavailability of Sublingual Buprenorphine, J. Clin. Pharmacol., 37: 31–37 (1997).

Mucklow, J. C., The Use of Saliva in Therapeutic Drug Monitoring, The Drug Monit., 4, 229 (1982).

Paxton, J. W., Measurement of Drugs in Saliva, Methods Find. Exp. Clin. Phamacol., 1, 11 (1979).

Samyn, N., et al., Analysis of Drugs of Abuse in Saliva, Forensic Science Review, 11(1): 1–17 (1999).

Schramm, W., et al., Drugs of Abuse in Saliva: A Review, J. Anal. Toxicol., 16(1): 1–9 (1992).

Tenuvuo, J., ed., Human Saliva: Clinical Chemistry and Microbiology, CRC Press, Boca Raton, 2: 177–201 (1989).

* cited by examiner

Primary Examiner—Lyle A. Alexander
(74) Attorney, Agent, or Firm—Lyon & Lyon LLP

(57) ABSTRACT

A device for measuring, concurrently from the same sample solution, the pH and presence or quantity of an analyte in the solution. The pH and analyte measuring sections of the invention are contained within the same holding structure.

57 Claims, 7 Drawing Sheets

DEVICE FOR DETECTING ANALYTES RELATED TO SAMPLE PH

BACKGROUND OF THE INVENTION

1. Field of the Invention

This invention relates to chemical analysis tests, and, in particular, a device for detecting the presence or quantity of analytes while also measuring the pH of sample solutions containing the analytes.

2. Background

The presence or quantity of specific molecules or substances ("analytes") in a solution can be determined through several known means, such as immunoassays or non-immunoassays. Depending on the nature of the assay, an active reagent is chosen from a group of reagents that are reactive with the analyte. Such reactive reagents include substances that react with the analyte, enzymes or enzymatic substrates of the analyte, or binding reagents of the analyte, such as antibodies or antigens.

Knowledge of the presence or quantity of analytes contained in bodily fluids is especially useful. Among other things, results of analyte testing can be used to diagnose medical conditions and to measure the concentration of drugs or toxic substances in a human or animal subject. Analyte test results can also be used to monitor appropriate levels of therapeutic agents or for other purposes.

In some situations, the presence or quantity of the analyte depends upon the pH of the solution. pH can be measured in a variety of different ways, including via color changes in organic compounds. Such compounds include methyl red, methyl orange, bromphenol blue, etc. When the presence of certain drugs, such as cocaine or methamphetamine, are assayed from saliva, the pH can assist the person administering the test in correlating the cocaine or methamphetamine in the saliva to the blood levels of the drug. See Malamud, D., Saliva as a Diagnostic Fluid, *Br. Med. J.* 305: 207–208 (1990); Mandel, I. D., The Diagnostic Uses of Saliva, *J. Oral Pathol. Med.,* 19: 119–125 (1990); Mandel, I. D., "Salivary Diagnosis: Promises, Promises," in Malamud, D. and Tabak, L. (Eds.) *Saliva as a Diagnostic Fluid,* Vol. 694: Annals of the New York Academy of Sciences, New York: The New York Academy of Sciences (1993), pp. 1–8; Kopecky, E. et al., Correlation of Morphine Sulfate in Blood Plasma and Saliva in Pediatric Patients, *Ther. Drug Monitoring,* 19 no. 5: 530–534 (1997); Leonard, J., et al., Correlation of Buccal Mucosal Transudate Collected with a Buccal Swab and Urine Levels of Cocaine, *J. Addictive Beh.,* 13 no. 1: 27–31 (1994); Mendelson, J., et al., Bioavailability of Sublingual Buprenorphine, *J. Clin. Pharm.,* 37:31–37 (1997). Such correlation of saliva concentrations to blood levels is important in situations such as detoxification, medical monitoring situations or in law enforcement situations.

Presently, blood levels of specific drugs are usually determined through invasive methods, such as venipuncture or finger-stick. The disadvantages of such invasive methods include the need for trained medical personnel, sterilization, discomfort, length of time required, prevention of contact with the blood by the phlebotomist and any other handlers, frequent multiple attempts at obtaining an appropriate sample. Consequently, a device that can use other bodily fluids and correlate them to blood levels represents a significant advancement over previous devices.

SUMMARY OF THE INVENTION

This invention involves a device for the concurrent measurement of pH and an analyte in solution where the presence or quantity of the analyte is related to the pH of the solution. Such solutions could include, but are not limited to, saliva, urine, whole blood, serum plasma, mucous or mixtures of other substances in liquid. The device is a single unit that contains a pH measurement section, an assay section, and a color coded pH comparison section that allows the pH to be interpreted. The simplicity of the device and the ability to quickly and accurately make appropriate measurements with pH correlation is a significant improvement over previous devices.

DETAILED DESCRIPTION OF THE PREFERRED EMBODIMENTS

Figure 1:
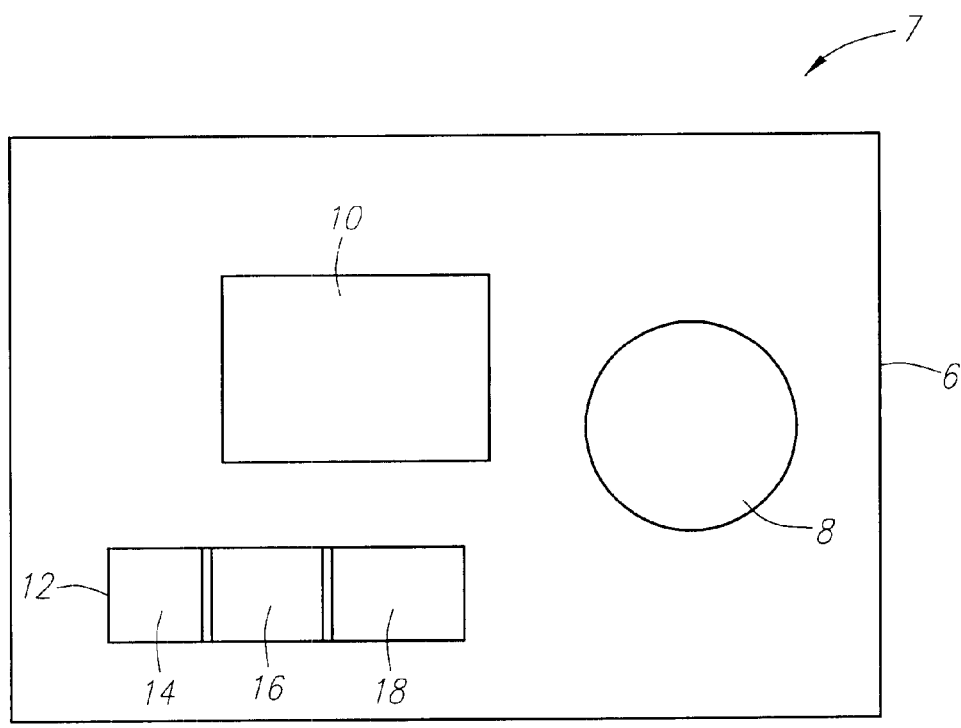
FIG. 1 depicts one embodiment of the invention that uses a membrane containing reagents for detecting an analyte.
Figure 2:
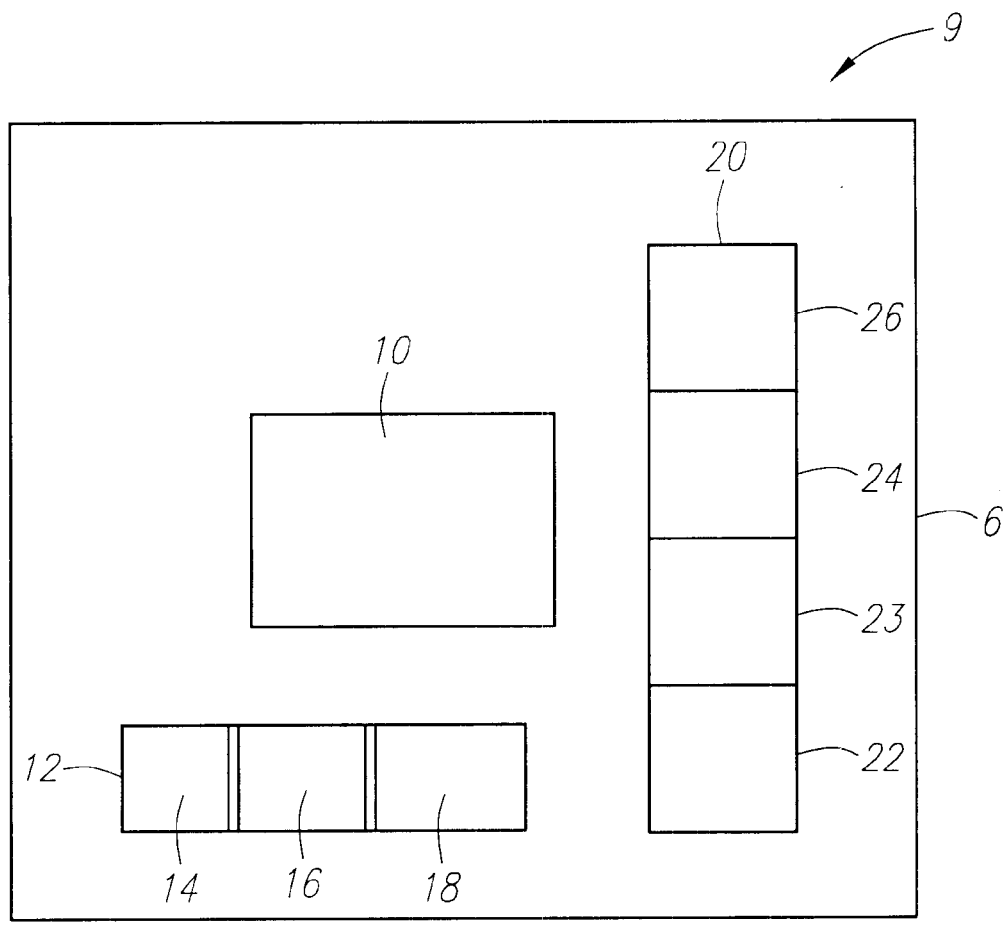
FIG. 2 depicts a different embodiment of the invention that utilizes a lateral flow immunoassay for detecting an analyte.

As shown in FIG. 1 and FIG. 2, a combination pH and analyte measuring device 7 or 9 is contained within a single holding structure 6. The device 7 or 9 is preferably made from a non-toxic, disposable material that prevents subsequent contamination with toxic substances or potentially infectious body fluids after disposal.

In one embodiment of the invention, there is an assay section 8 or 20 for measuring the presence or quantity of an analyte in a sample solution and also a section 10 for measuring the pH of the same solution. In addition, there is a color coded pH comparison chart 12 contained within the holding structure. Both the assay section 8 or 20 and the pH section 10 are housed within the same holding structure 6. The assay section 8 or 20 contains at least one active reagent for the testing of the analyte. Depending on the nature of the assay, the active reagent is chosen from a group of reagents that are reactive with the analyte. Such reactive reagents include reactive chemicals of the analyte, enzymes or enzymatic substrates of the analyte, and binding agents of the analyte, such as antibodies or antigens.

For example, a flow-through immunoassay comprises a porous membrane having a binding reagent immobilized on the membrane. An absorbent material is placed on one side of the membrane. When a sample containing an analyte is applied to the membrane, the sample flows through the membrane by capillary movement. The analyte is then bound to the binding reagent.

A flow-through immunoassay further comprises applying a tracer that is another binding reagent of the analyte with a label for detecting the bound analyte. The binding reagents of the membrane and tracer are selected from a group consisting of antibodies, antigens, protein A, protein G, receptor proteins, etc. The label can be selected from a group of detectable substances, including enzymes, radioactive isotopes, and particular color particles. Suitable membranes include glass fiber, polyvinylidene difluoride, polycarbonate, nitrocellulose, nylon, etc. See U.S. Pat. No. 5,155,022.

Reagents for the assay of analytes can be placed at the assay section by different means, including embedding, absorption, and covalent bond formation between the reagent and the supporting material, which are familiar to those skilled in the art. See U.S. Pat. Nos. 5,602,040; 5,559,041; 4,943,522; and 5,591,645.

Measuring the signal intensity of the test area with an instrument can make quantitative or semiquantitative assays of analytes in the sample. Depending on the property of the label of the tracer, a measuring instrument that is capable of reading the signal of the tracer is chosen for the purpose. Such instrument may be a gamma counter for radioactive isotope labeled tracers, a fluorescence reader for fluorophore labeled tracers, and spectrophotometer for reading the reflection of colored assay areas in assays involving particular particle labeled tracers. A calibration curve/dose response curve of the assay can be used for calculating the analyte concentration.

For assays employing particular particle labeled tracers, the resulting color test areas can be read visually to give semi-quantitative determinations of the analytes made through comparisons to a color chart. Different intensity color areas are printed on a color chart. The color intensity of the test area is matched with the color area on the chart, which corresponds to a value of the analyte quantity in the sample.

The pH section 10 involves utilizing organic compounds that have varied color changes in solutions of different pH. Such compounds include methyl red, methyl orange, bromphenol blue, etc. These reagents can be placed in the pH test unit as a solution or dry powder. The dry reagents can be imbedded into a porous matrix as a pH strip that is commercially available.

The pH test section 10 and the assay section 8 or 20 are positioned within the same holding structure 6. The pH test section 10 and the assay section 8 or 20 are arranged within the holding structure to allow relatively simultaneous performance of both the pH test and assay analysis. The material for the holding structure 6 may be chosen from a group of solid materials, including plastic, metal, cellulose, or other similar materials known to those skilled in the art.

In one preferred embodiment of the invention 7, the sample solution is placed on a membrane in the assay section 8 that contains reagents for detecting the analyte. The sample is also placed on a pad containing reagents for measuring pH 10. The pH chart 12 has three different indicator areas 14, 16, 18. Each color of the indicator area represents one pH value. The pH of the sample solution is measured by matching the color observed on the pH pad 10 with that of the pH chart 12.

In another preferred embodiment of the invention 9, the assay section of the device is a lateral flow immunoassay strip 20. The lateral flow assay section comprises a bibulous assay strip having four zones: a sample addition zone 22, a tracer zone 23, a test zone 24, and a reagent-receiving zone 26. A movable tracer is supported at tracer zone 23. A binder is immobilized at test zone 24.

An assay sample applied to sample addition zone 22 will flow through zone 23 and zone 24 until being absorbed at receiving zone 26 by capillary action. The presence or quantity of the analyte in the sample is determined by measuring the presence or quantity of tracer bound at test zone 24.

There are three forms of lateral flow assay: sandwich assay and two forms of competitive assay.

In one preferred embodiment, the lateral flow immunoassay is a sandwich immunoassay with the tracer at zone 23 and an immobilized binder at zone 24 being capable of binding the analyte. If the sample contains the analyte, the analyte will bind with the tracer at the tracer zone 23, and the binder at the test zone 24 will then capture the analyte-tracer complex. A detectable amount of analyte is the amount of analyte capable of producing a detectable amount of tracer signal at test zone 24. If the sample does not contain the analyte, the tracer will flow through test zone 24 and no detectable amount of tracer will be bound at test zone 24.

In another preferred embodiment, the lateral flow immunoassay is a competitive immunoassay, with the tracer being a labeled analyte or an analogue of the analyte, and the binder being a binder of both the analyte and the tracer. The analyte and the tracer compete for binding sites at test zone 24. The quantity of tracer bound at test zone 24 is inversely proportional to the quantity of analyte in the sample solution.

In another preferred embodiment, the lateral flow immunoassay is a competitive immunoassay, with the tracer being a labeled binding reagent of the analyte, and the binder at test zone 24 being an analogue of the analyte that also binds the tracer. The analyte in the sample competes with the binder at test zone 24 for binding sites of the tracer. The quantity of tracer bound at test zone 24 is inversely proportional to the quantity of analyte in the sample solution.

The binding reagents in a lateral flow immunoassay are selected from a group consisting of antibodies, antigens, protein A, protein G, receptor proteins, etc. The label can be selected from a group of detectable compounds, including enzymes, radioactive isotopes, and particular color particles. Suitable bibulous materials include glass fiber, polyvinylidene difluoride, polycarbonate, nitrocellulose, nylon, etc.

Reagents for the assay of analytes can be placed at the test zone by different means, including embedding, absorption, and covalent bond formation between the reagent and the supporting material, which are familiar to those skilled in the art.

In another preferred embodiment of the invention, a hydrophobic divider separates the agents of the pH test section 10 and the assay section 8 or 20. The assay protocol of this embodiment comprises applying the sample solution separately to both the pH test section 10 and assay section 8 or 20. In another preferred embodiment of the invention, there is no hydrophobic barrier between the reagents of the pH test section 10 and the assay section 8 or 20 so that a solution applied to one zone of the device will flow to both the pH test section and the assay section simultaneously or sequentially.

In another preferred embodiment of the invention 70, the holding structure 72 contains a pH section 82, a sample application section 84 and an assay measurement section 75. The assay measurement section is divided into a test section 76 and a control section 74. A color chart 78 is provided to compare the color intensity that shows in the test section 76 to known quantities of an analyte. A pH chart 80 is provided to compare the color that appears in the pH section 82 with the chart 80.

The result of the detected analyte may be calibrated using a formula involving the measured pH of the sample solution. For example, the presence or quantity of certain drugs in saliva is dependent upon the pH of the saliva. Saliva testing is useful because non-protein bound plasma fractions of drugs can easily be measured in saliva. When saliva samples are assayed to estimate the blood concentration of the drugs, the saliva drug concentrations can be converted to blood drug concentrations with the formula involving the pH value of the saliva sample. Schram, W., et al. Drugs of Abuse in Saliva: A Review, *J. Anal. Toxicol.* 16(1): 1–9 (1992); Wamyn, N., et al., Analysis of Drugs of Abuse in Saliva, *Forensic Science Review* 11(1): 1–17 (1999).

The majority of drugs, such as cocaine, enter saliva from plasma predominantly by passive diffusion of the unbound, non-ionized moiety down a concentration gradient of the drug (the ionized forms also diffuse across the saliva/plasma barrier but very slowly). Thus, at equilibrium, the concentration of the non-ionized drug will be the same on both sides of the membrane. The hydrogen ion concentration is therefore the most relevant factor that affects drug secretion into saliva.

The extent of ionization of a weak electrolyte is determined by its pKa and the pH of the solution. The following formula is derived from the Henderson-Hasselbalch equation (Mucklow, J. C., The use of Saliva in Therapeutic Drug Monitoring (review), *The Drug Monit.*, 4, 229, 1982; Paxton, J. W., Measurement of Drugs in Saliva, *Methods Find. Exp. Clin. Pharmacol.*, 1, 11, 1979); Tenovuo, J. ed., *Human Saliva: Clinical Chemistry and Microbiology*, CRC Press, Boca Raton, 2: 177–201 (1989); Jusko, et al., Pharmacokinetic Principles of Drug Distribution in Saliva, *Ann. N.Y. Acad. Sci.*, 694: 36–47 (1993):

$$10^{(pH-pKa)}=[D']/[HD]$$

Where D' is the ionized form of the drug and HD is the non-ionized form of the drug.

For a given drug, the pKa is fixed. Therefore, the pH of the solution determines the extent of ionization of the drug. Thus, the predicted ratio of drug concentration in saliva and drug concentration in plasma can be calculated knowing the saliva and plasma pH, and the pKa of the drug from the following:

Weak acids: $S/P=[1+10^{(pHs-pKa)}]/[1+10^{(pHp-pKa)}]$

Weak Bases: $S/P=[1+10^{(pKa-pHs)}]/[1+10^{(pKa-pHp)}]$

Where S/P is the saliva drug concentration/plasma drug concentration, pHs is saliva pH, pHp is plasma pH, and pKa is the pKa of the drug.

Since the pH of healthy human plasma is relatively stable, the pH of saliva is the most important factor affecting $[A]_s/[A]_p$ ratio. In many cases it is not necessary to test the pH of plasma to calculate the predicted plasma drug level.

Although saliva drug concentration levels can be correlated to plasma levels, saliva assay results can also be useful within themselves. For example, the cut-off level for determining whether a person is under the influence of cocaine can be set in connection with the pH of the saliva sample.

Saliva testing has several advantages over invasive blood testing. Saliva testing is not painful, is virtually risk free to all involved, is simple and quick, and is more economic. Saliva testing in conjunction with saliva pH testing is advantageous over saliva testing alone because it allows accurate prediction of blood levels of analytes based on saliva testing result and saliva pH. The saliva and pH testing device claimed in this application is a single holding structure that contains both the assay section and the pH testing section. Such a single unit that contains both tests has several advantages over separate testing of saliva for analytes and pH. First, the single device is more convenient for use than two separate tests. In addition, pH can be tested immediately before it rises due to release of dissolved carbon dioxide.

One preferred embodiment of the invention includes a kit that contains the device consisting of the holding structure, the pH section, the pH chart, the assay section and instructions for determining the blood concentration of the analyte from the measured pH and the analyte concentration of the saliva sample.

Figure 3:
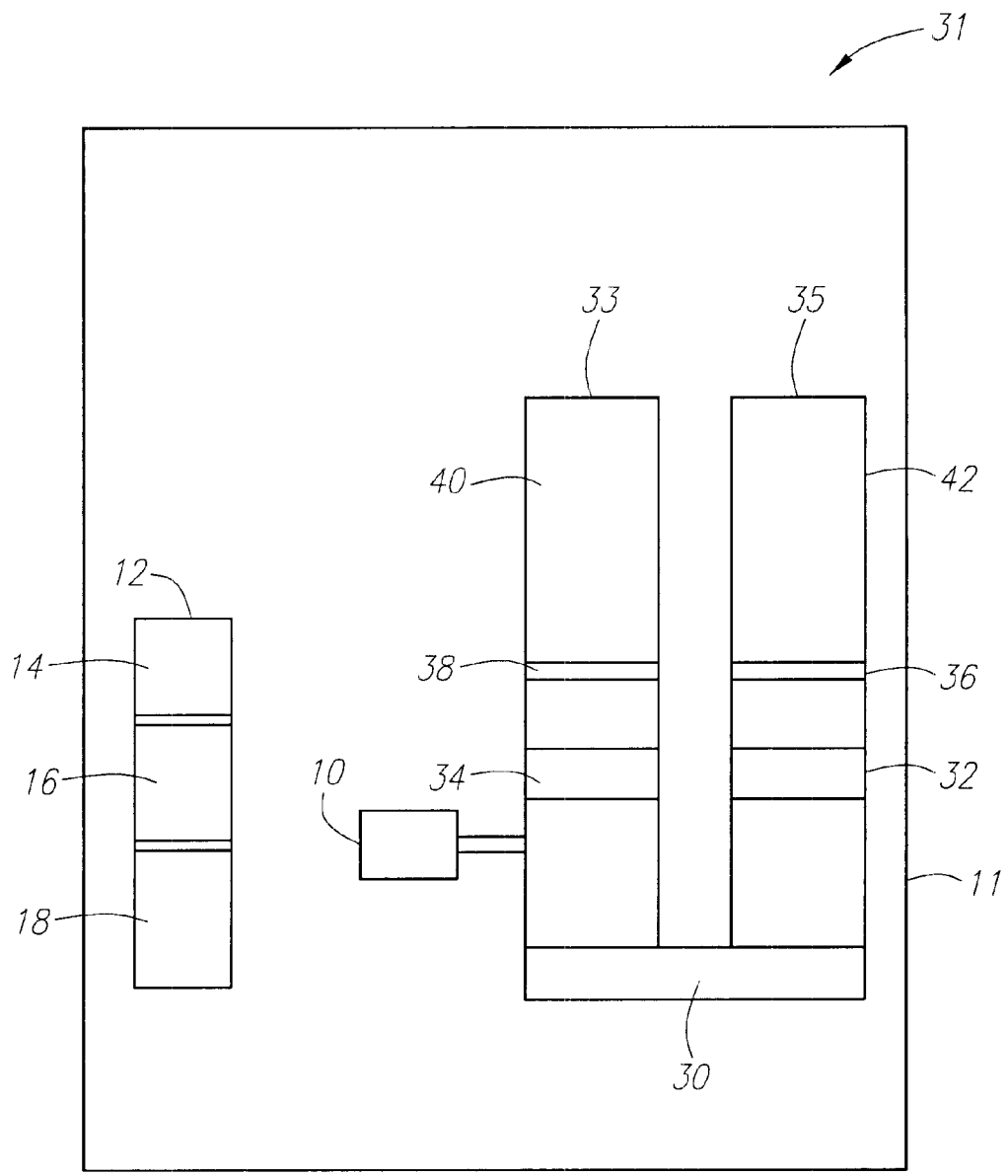
FIG. 3 depicts one embodiment of the invention where the pH of the specimen and the presence or quantity of two analytes in one sample solution can be determined in one unit on two separate assay strips.

Another preferred embodiment of the invention allows the pH and analytes of several different drugs to be tested in one unit from the same sample solution. For example, the presence or quantity of cocaine, marijuana and/or other drugs can be tested from one saliva sample in one single unit, as depicted in FIG. 3. In such a multi-drug testing unit 31, the sample is applied to an application zone 30, which is in flow communication with two separate assay strips 33 and 35 and a pH section 10. The sample flows by capillary action through a tracer zone on each strip 32 and 34 and continues to two separate assay zones 36 and 38 where the tracer is bound depending on the presence or quantity of the analyte in the assay sample. Non-bound portions of the sample then flow into receiving zones 40 and 42. As with the other embodiments, a pH comparison section 12 is present. All of the elements of both assay strips 33 and 35, the application zone 30, the pH section 10, and the pH comparison chart 12 are contained within the same holding structure 11. This embodiment can be altered to allow for the addition of more assay strips to accommodate tests for more than two drugs.

Figure 4:
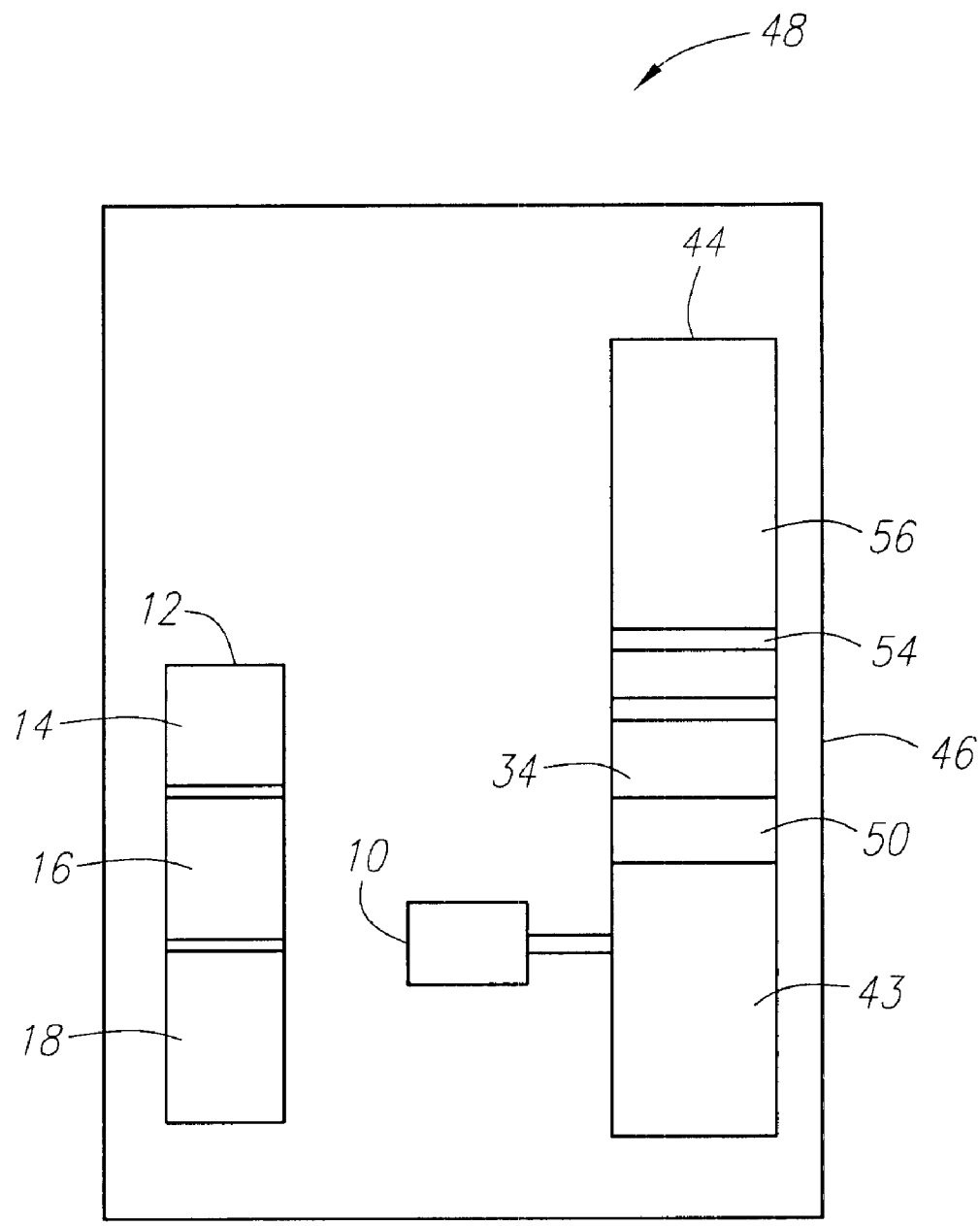
FIG. 4 depicts another embodiment of the invention where the pH and analytes of two different drugs can be tested on the same assay strip.

FIG. 4 illustrates another embodiment 48 used for multi-drug testing that uses a single assay strip 44. The sample is applied to the application zone 43 and then flows to the tracer zone 50. The analytes then bind to either assay zone 52 or assay zone 54, depending on which drug is being bound at that assay area. The unbound portion of the sample then flows into the receiving zone 56. The pH section 10 is in flow communication with the assay strip 44. All components of the assay strip 44, the pH section 10, and the pH comparison chart 12 are contained within the same holding structure 46. This embodiment can be altered to allow for the addition of more assay areas on the strip to accommodate tests for more than two drugs.

Figure 5:
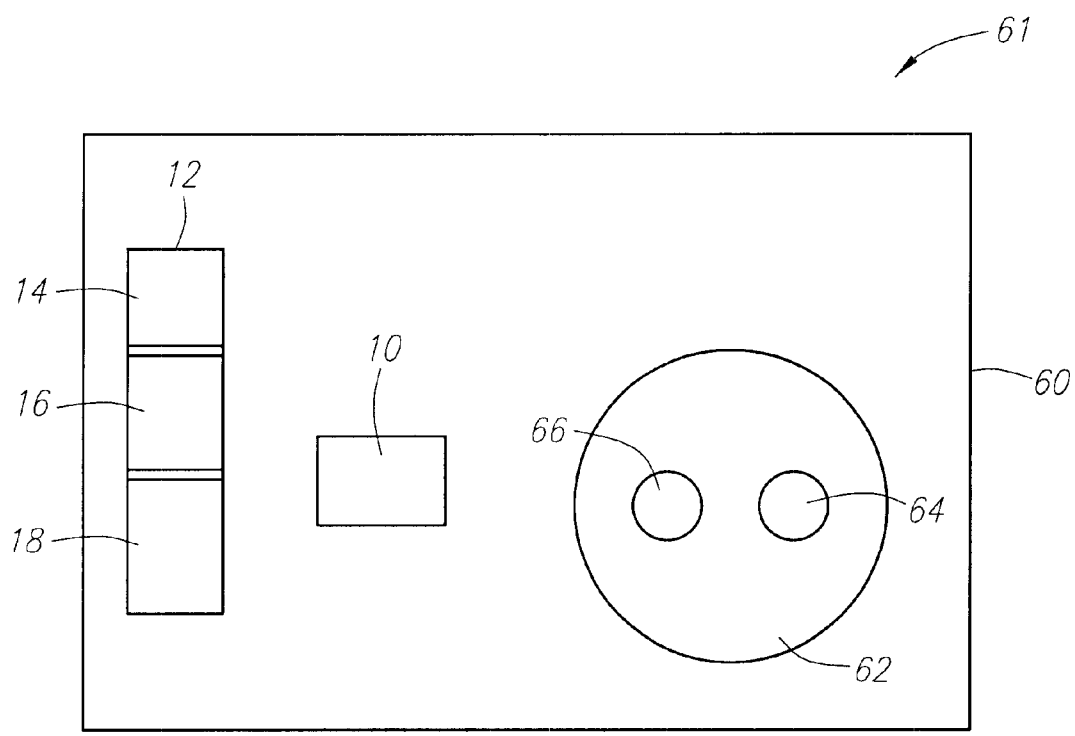
FIG. 5 depicts another embodiment of the invention where the pH and analytes of two different drugs can be tested on a flow-through assay device.

Another embodiment of the invention that allows for multi-drug testing is a flow-through assay device as depicted in FIG. 5. The sample solution is placed on the assay section 62 and flows to two assay zones 64 and 66. Zone 64 is the binding zone for one drug, and zone 66 is the binding zone for the second drug. Additional binding zones for other drugs can be added if needed. A labelled tracer that is another binding reagent of the analyte is applied to assay zone 64 or 66, and it makes the bound analyte detectable. In this embodiment, a separate sample is applied to the pH section 10. All components of the device, including the pH comparison chart, are contained within a single holding structure 60.

EXAMPLE 1

To detect cocaine and/or other drugs, saliva would be collected from a person using a saliva collection device, such as the device described in U.S. patent application Ser. No. 09/183,295, Tatum et al., allowed Nov. 14, 1999. The saliva would then be transferred from the collection device to the sample addition zone 22 of the single assay strip 20. The solution then migrates to the pH section 10 and the tracer zone 23, then to the assay membrane test zone 24. The pH value of the sample can be read at approximately 30 seconds after application, and the drug test result can be read on the assay test zone 24 approximately five minutes after sample application.

EXAMPLE 2

Figure 6:
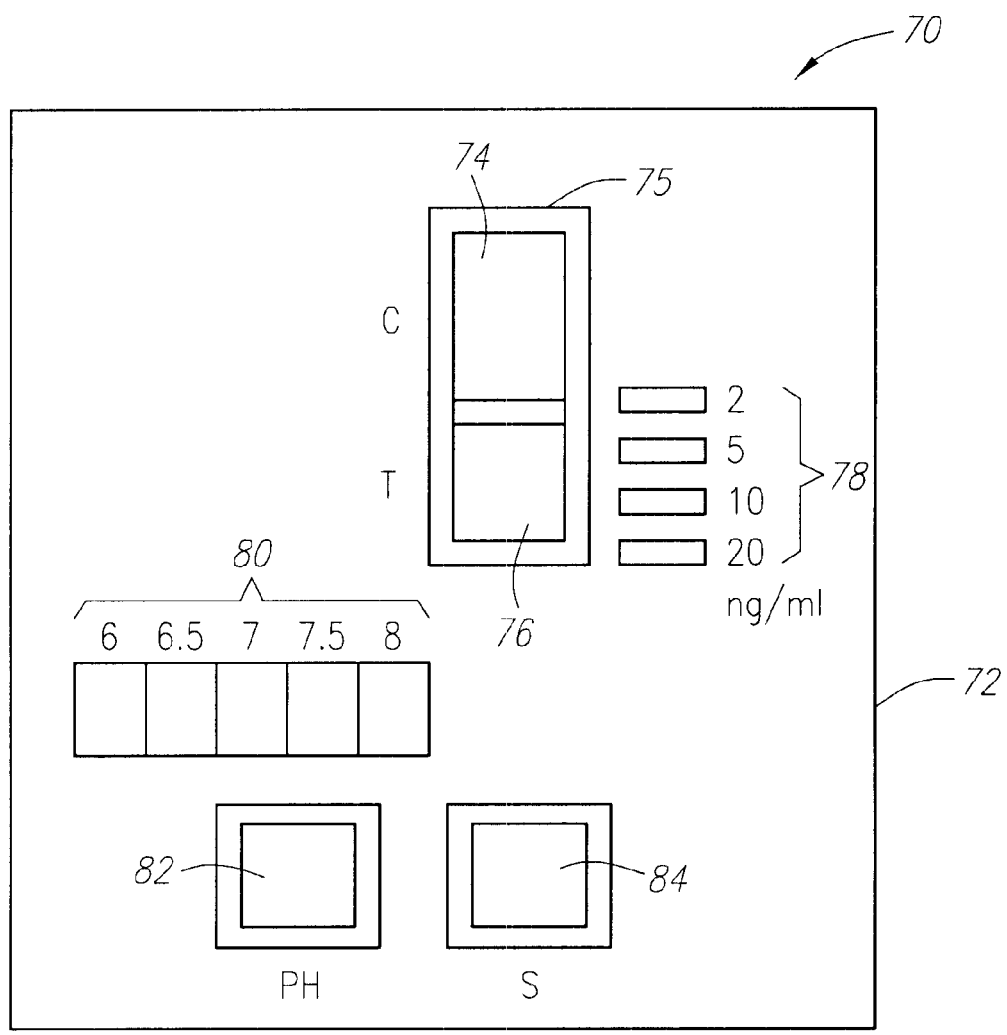
FIG. 6 depicts a preferred embodiment of the device that contains a color chart designed to aid in semi-quantitatively determining the amount of a drug in saliva.
Figure 7:
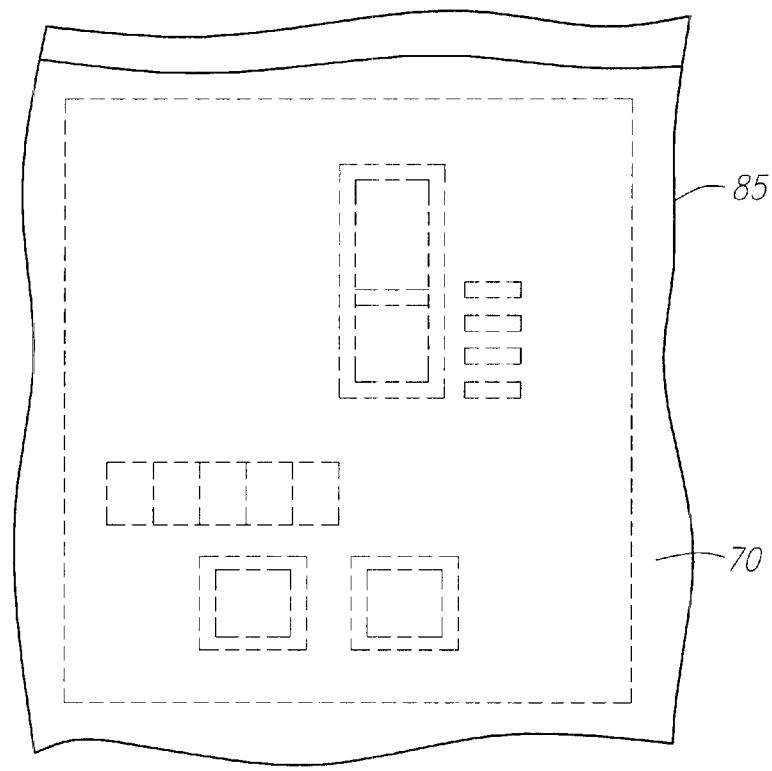
FIG. 7 depicts a wrapper surrounding the holding structure within a kit.
Figure 8:
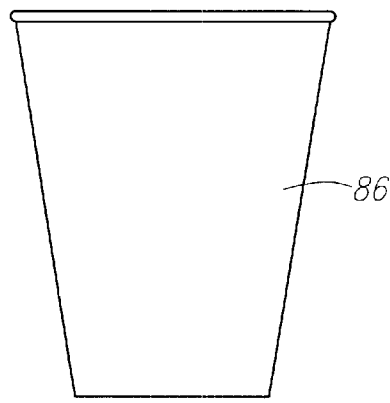
FIG. 8 depicts a sample cup that can be included in a kit.
Figure 9:
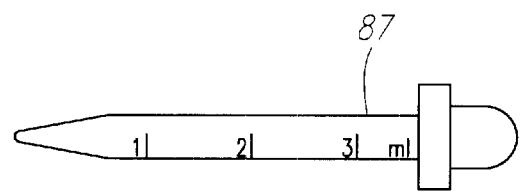
FIG. 9 depicts a dropper that can be used to place saliva drops on the testing device of the kit.

The following is an example of instructions that could be included in a preferred embodiment of a kit. The device, or cassette of the kit, is depicted in FIG. 6:

This test kit is for use in testing cocaine in a saliva sample and deriving the corresponding concentration in plasma. Since cocaine secretion from blood to saliva strongly depends on the pH of saliva, the value is factored into the calculation of plasma cocaine concentration from measured saliva cocaine concentration. A semi-quantitative result from plasma cocaine concentration is obtained at the end of the assay.

Assay principle

Each rapid oral fluid test cassette 70 included in this test kit consists of a lateral flow assay strip, a color intensity chart 78, a pH test section 82, and a pH chart 80. The lateral flow assay strip consists of color dye labeled cocaine antibody and a nitrocellulose membrane coated with cocaine-Bovine Serum Antibody ("BSA") conjugate. When a saliva sample is applied to the sample section of the cassette, the saliva sample will migrate by capillary movement to the dye-antibody zone and the cocaine-BSA membrane zone. If the sample tested is negative, the dye-antibody will bind with the membrane cocaine-BSA conjugate to form a red band on the membrane.

If the sample tested contains cocaine, cocaine in the sample will bind with the dye-antibody, and thus the binding between the dye-antibody and the membrane cocaine-BSA is prevented. The unbound dye-antibody will migrate away from the membrane to an absorbent pad. As a result, the intensity of the color band appearing on the membrane is inversely proportional to the concentration of cocaine in the saliva sample. A semi-quantitative result of cocaine concentration in the saliva sample is achieved by comparing the color band with a color intensity chart.

A control section 74 is also included on the assay membrane 75. A binding reagent of the dye-antibody conjugate is coated at the control section 74 (C area), which binding reagent will bind the dye-antibody conjugate regardless of the presence of cocaine in the assay sample.

A pH section 82 in the cassette, is in flow communication with the sample application zone 84 of the lateral flow assay strip. A portion of the saliva sample applied to the sample section 84 will flow to the pH section 82. The pH section 82 contains methyl red and bromphenol blue, which change colors according to the pH of the sample solution. The pH of the saliva sample is determined by comparing the color of the pH section 82 to the colors on the pH chart 80.

Plasma concentration of cocaine is calculated by correlating the pH of the saliva sample with saliva concentration of cocaine. A list of cocaine saliva/plasma ratio (S/P ratio) has been provided with their corresponding saliva pH values.

Materials provided

1. Rapid oral fluid test-cocaine cassette in wrapper
2. Sample cup
3. Dropper
4. Instruction Materials required and not provided with this kit 1 Timer or watch
2 Pencil or marker Assay procedure
Sample collection and handling 1. Collect at least 1 ml of fresh saliva without stimulation into the sample cup 86.
2. If the sample is not to be tested immediately, freeze the sample at <−15° C.

Assay procedure

1. Open the aluminum foil pouch 85 of the cassette test device and lay the device on a flat surface.
2. Remove saliva from the sample cup 86 using the dropper 87.
3. Apply 4 drops of saliva sample to the "s" window of the cassette device by holding the dropper straight above the window.
4. Read the pH test after 30 seconds and cocaine test results at five minutes (see result interpretation).

Assay validation

1. If the pH pad is wet at 30 seconds and there is a color band present at the "C" window at the end of 5 minutes, the test is valid.
2. If, at the end of 30 seconds, the pH pad is not wet or at the end of 5 minutes there is no color band present at the "C" window, the assay is invalid. In that case, the sample should be re-tested on a new cassette.

Result interpretation 1. pH
   a) Compare the color of the pH section with the pH chart 30 seconds after the sample is applied to the cassette.
   b) Write down the pH value of the saliva sample.
2. Cocaine concentration in the saliva sample
   a) 5 minutes after application, compare the color band in the "T" window with the color intensity chart.
   b) Write down the cocaine concentration by the color area that is closest to the color band of the "T" window in intensity.
   c) If the intensity of the resulting color band is in between two color areas by the color intensity chart, estimate cocaine concentration by averaging the two concentration values by the two color areas.
   d) If the intensity of the resulting color band is higher than the most intense color are of the color intensity chart, cocaine concentration in the saliva sample is <2 ng/ml or the result is negative.
   e) If there is no color band present at the "IT" window, cocaine concentration in the saliva sample is >20 ng/ml.

Calculation of plasma cocaine concentration

If the test result of cocaine concentration is NOT negative, proceed to estimate plasma cocaine concentration.

1. Look up the S/P ratio correlate to the pH of the saliva sample from Table 1.

TABLE 1

Saliva/plasma cocaine concentration ratio (S/P) with saliva pH

| Saliva pH | S/P |
|---|---|
| 6.5 | 7.47 |
| 7.0 | 2.40 |
| 7.5 | 0.75 |
| 8.0 | 0.24 |
| 8.5 | 0.10 |

Calculation

Plasma cocaine concentration in ng/ml=Saliva cocaine concentration $_{13}$ ng/ml÷S/P ratio.

The antibody used in this assay has less than 5% cross-reactivity with benzoylecgonine as compared with cocaine. No significant cross-reactivity was found with tetrahydrocannabinols, phencyclidine, methamphetamine, morphine, codeine, or ethanol.

Cautions
1. For in vitro diagnosis use only.
2. Dispose used devices as biohazards.
3. The test result is for reference only. Positive result needs to be confirmed with GC/MS or other confirmatory methods.

REFERENCES

1. W. Schram, et al, "Drugs of abuse in Saliva: A Review," J. Anal. Toxicol. 16(1):1–9, 1992
2. N Wamyn, et al, "Analysis od Drugs of Abuse in Saliva" Forensic Science Review, 11(1):1–17, 1999

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A device for concurrent measurement of pH and detection of an analyte(s) in solution, comprising:
   a holding structure;
   a pH measuring section within the holding structure;
   an analyte measuring section within the holding structure; and
   wherein the presence or quantity of the analyte is dependent on the pH of the solution.

2. The device of claim 1 wherein the detection of the analyte(s) may be either qualitative or quantitative.

3. The device of claim 1 further comprising a pH chart within the holding structure.

4. The device of claim 1 further comprising a color intensity chart within the holding structure for measuring analyte results.

5. A device for concurrent measurement of pH and detection of an analyte(s) in solution, comprising:
   a holding structure;
   a pH measuring section within the holding structure;
   an analyte measuring section within the holding structure; and
   wherein the analyte is cocaine.

6. A device for concurrent measurement of pH and detection of an analyte(s) in solution, comprising:
   a holding structure;
   a pH measuring section within the holding structure;
   an analyte measuring section within the holding structure; and
   wherein the analyte is methamphetamine.

7. The device of claim 1 wherein the solution is saliva.

8. The device of claim 1 wherein the holding structure is composed of a material that will not interact with the sample solutions or analytes therein.

9. The device of claim 8 wherein the holding structure is disposable.

10. The device of claim 9 wherein the holding structure is composed of non-toxic materials.

11. The device of claim 10 wherein the holding structure is designed to prevent contamination after disposal of toxic substances or potentially infectious body fluids.

12. The device of claim 1 wherein the holding structure is composed of a material selected from the following group consisting of plastic, metal, and cellulose.

13. The device of claim 8 wherein the holding structure is composed of a material selected from the following group consisting of plastic, metal, and cellulose.

14. The device of claim 9 wherein the holding structure is composed of a material selected from the following group consisting of plastic, metal, and cellulose.

15. The device of claim 10 wherein the holding structure is composed of a material selected from the following group consisting of plastic, metal, and cellulose.

16. The device of claim 11 wherein the holding structure is composed of a material selected from the following group consisting of plastic, metal, and cellulose.

17. The device of claim 1 wherein the pH measurement section is composed of an organic compound that changes colors based on the pH of the sample solution.

18. The device of claim 1 wherein the pH measurement section is composed of an organic compound that changes colors based on the pH of the sample solution from the following group consisting of methyl red, methyl orange, and bromphenol blue.

19. The device of claim 1 wherein there is a hydrophobic barrier between the pH measurement section and the analyte measuring section.

20. The device of claim 1 wherein there is not a hydrophobic barrier between the pH measurement section and the analyte measuring section so that sample solutions applied to one section will flow to the other section.

21. The device of claim 1 wherein the analyte measuring section consists of a lateral flow immunoassay strip divided into four zones.

22. The device of claim 21 wherein the four zones consist of a sample addition zone, a tracer zone, a test zone, and a receiving zone.

23. A device for concurrent measurement of pH and detection of an analyte(s) in saliva, comprising:
   a holding structure;
   a pH measuring section within the holding structure;
   an analyte measuring section within the holding structure; and
   wherein the presence or quantity of the analyte is dependent on the pH of the saliva.

24. The device of claim 23 wherein the detection of the analyte(s) may be either qualitative or quantitative.

25. The device of claim 23 further comprising a pH chart within the holding structure.

26. The device of claim 23 further comprising a color intensity chart within the holding structure for measuring analyte results.

27. A device for concurrent measurement of pH and detection of an analyte(s) in saliva, comprising:
a holding structure;
a pH measuring section within the holding structure;
an analyte measuring section within the holding structure; and
wherein the analyte is cocaine.

28. A device for concurrent measurement of pH and detection of an analyte(s) in saliva, comprising:
a holding structure;
a pH measuring section within the holding structure;
an analyte measuring section within the holding structure; and
wherein the analyte is methamphetamine.

29. A device for concurrent measurement of pH and the detection of cocaine in saliva, comprising:
a holding structure;
a pH measuring section within the holding structure; and
a cocaine measuring section within the holding structure.

30. The device of claim 29 wherein the detection of cocaine may be either qualitative or quantitative.

31. The device of claim 29 further comprising a pH chart within the holding structure.

32. The device of claim 29 further comprising a color intensity chart within the holding structure for measuring cocaine results.

33. A device for concurrent measurement of pH and detection of methamphetamine in saliva, comprising:
a holding structure;
a pH measuring section within the holding structure; and
a methamphetamine measuring section within the holding structure.

34. The device of claim 33 wherein the detection of methamphetamine may be either qualitative or quantitative.

35. The device of claim 33 further comprising a pH chart within the holding structure.

36. The device of claim 33 further comprising a color intensity chart within the holding structure for measuring methamphetamine results.

37. A kit for determining blood concentration of an analyte(s) using a non-blood sample, comprising:
a holding structure;
a pH measuring section within the holding structure;
an analyte measuring section within the holding structure wherein the presence or quantity of the analyte is dependent on the pH of the sample;
a pH chart;
a color intensity chart for measuring analyte results; and
instructions for determining the blood concentration of an analyte from the measured pH and the analyte concentration in a sample solution.

38. The kit of claim 37 wherein the non-blood sample is saliva.

39. A kit for determining blood concentration of an analyte(s) using a non-blood sample, comprising:
a holding structure;
a pH measuring section within the holding structure;
an analyte measuring section within the holding structure;
a pH chart;
a color intensity chart for measuring analyte results;
instructions for determining the blood concentration of an analyte from the measured pH and the analyte concentration in a sample solution; and
wherein the analyte is cocaine.

40. A kit for determining blood concentration of an analyte(s) using a non-blood sample, comprising:
a holding structure;
a pH measuring section within the holding structure;
an analyte measuring section within the holding structure;
a pH chart;
a color intensity chart for measuring analyte results;
instructions for determining the blood concentration of an analyte from the measured pH and the analyte concentration in a sample solution; and
wherein the analyte is methamphetamine.

41. The kit of claim 37 further comprising a sample cup in which to store the sample.

42. The kit of claim 37 further comprising a dropper.

43. The kit of claim 37 further comprising a wrapper around the holding structure.

44. A kit for determining blood concentration of an analyte(s) using a saliva sample, comprising:
a holding structure;
a pH measuring section within the holding structure;
an analyte measuring section within the holding structure wherein the presence or quantity of the analyte is dependent on the pH of the sample;
a pH chart;
a color intensity chart for measuring analyte results; and
instructions for determining the blood concentration of an analyte from the measured pH and the analyte concentration in a sample solution.

45. A kit for determining blood concentration of an analyte(s) using a saliva sample, comprising:
a holding structure;
a pH measuring section within the holding structure;
an analyte measuring section within the holding structure;
a pH chart;
a color intensity chart for measuring analyte results;
instructions for determining the blood concentration of an analyte from the measured pH and the analyte concentration in a sample solution; and
wherein the analyte is methamphetamine.

46. A kit for determining blood concentration of an analyte(s) using a saliva sample, comprising:
a holding structure;
a pH measuring section within the holding structure;
an analyte measuring section within the holding structure;
a pH chart;
a color intensity chart for measuring analyte results;
instructions for determining the blood concentration of an analyte from the measured pH and the analyte concentration in a sample solution; and
wherein the analyte is cocaine.

47. The kit of claim 44 further comprising a sample cup in which to store the sample.

48. The kit of claim 44 further comprising a dropper.

49. The kit of claim 44 further comprising a wrapper around the holding structure.

50. A kit for determining blood concentration of methamphetamine using a saliva sample, comprising:
a holding structure;
a pH measuring section within the holding structure;
a methamphetamine measuring section within the holding structure;

a pH chart;

a color intensity chart for measuring methamphetamine results; and instructions for determining the blood concentration of methamphetamine from the measured pH and the methamphetamine concentration in a sample solution.

51. The kit of claim 50 further comprising a sample cup in which to store the sample.

52. The kit of claim 50 further comprising a dropper.

53. The kit of claim 50 further comprising a wrapper around the holding structure.

54. A kit for determining blood concentration of cocaine using a saliva sample, comprising:

a holding structure;

a pH measuring section within the holding structure;

a cocaine measuring section within the holding structure;

a pH chart;

a color intensity chart for measuring cocaine results; and instructions for determining the blood concentration of cocaine from the measured pH and the cocaine concentration in a sample solution.

55. The kit of claim 54 further comprising a sample cup in which to store the sample.

56. The kit of claim 54 further comprising a dropper.

57. The kit of claim 54 further comprising a wrapper around the holding structure.

\* \* \* \* \*